(12) United States Patent
Nakagawa (10) Patent No.: US 11,497,939 B2
(45) Date of Patent: Nov. 15, 2022

(54) METHOD FOR RECONSTRUCTING X-RAY CONE-BEAM CT IMAGES

(71) Applicant: Keiichi Nakagawa, Tokyo (JP)

(72) Inventor: Keiichi Nakagawa, Tokyo (JP)

(*) Notice: Subject to any disclaimer, the term of this patent is extended or adjusted under 35 U.S.C. 154(b) by 262 days.

(21) Appl. No.: 16/942,524

(22) Filed: Jul. 29, 2020

(65) Prior Publication Data

US 2021/0031057 A1  Feb. 4, 2021

(51) Int. Cl.
| | |
|---|---|
| *G06N 3/04* | (2006.01) |
| *A61N 5/10* | (2006.01) |
| *A61B 6/03* | (2006.01) |
| *G06T 11/00* | (2006.01) |
| *G06N 3/08* | (2006.01) |
| *A61B 6/00* | (2006.01) |

(52) U.S. Cl.
CPC ............ *A61N 5/1081* (2013.01); *A61B 6/032* (2013.01); *A61B 6/4085* (2013.01); *A61B 6/5282* (2013.01); *A61B 6/583* (2013.01); *A61N 5/1031* (2013.01); *A61N 5/1038* (2013.01); *A61N 5/1049* (2013.01); *A61N 5/1075* (2013.01); *G06N 3/04* (2013.01); *G06N 3/0454* (2013.01); *G06N 3/08* (2013.01); *G06T 11/005* (2013.01); *A61N 2005/1034* (2013.01); *A61N 2005/1061* (2013.01); *A61N 2005/1076* (2013.01)

(58) Field of Classification Search
CPC ..... A61B 6/032; A61B 6/4085; A61B 6/5282; A61B 6/583; A61N 5/1031; A61N 5/1038; A61N 5/1049; A61N 5/1075; A61N 5/1081; A61N 2005/1034; A61N 2005/1061; A61N 2005/1076; G06N 3/04; G06N 3/0454; G06N 3/08; G06T 11/005
See application file for complete search history.

(56) References Cited

U.S. PATENT DOCUMENTS

| | | | |
|---|---|---|---|
| 6,842,502 B2 * | 1/2005 | Jaffray | A61B 6/583 |
| | | | 378/65 |
| 2006/0002505 A1 * | 1/2006 | Saito | A61B 6/032 |
| | | | 378/4 |
| 2006/0008046 A1 * | 1/2006 | Ruhrnschopf | A61B 6/5282 |
| | | | 378/7 |
| 2006/0067464 A1 * | 3/2006 | Clinthorne | A61B 6/482 |
| | | | 378/38 |

(Continued)

FOREIGN PATENT DOCUMENTS

| | | | | |
|---|---|---|---|---|
| EP | 2009592 A2 * | 12/2008 | | G06T 11/005 |
| WO | WO-9901066 A1 * | 1/1999 | | A61B 6/027 |
| WO | WO-2007120744 A2 * | 10/2007 | | A61B 6/025 |

*Primary Examiner* — Mark R Gaworecki (57) ABSTRACT

An improved x-ray cone-beam CT image reconstruction by end-to-end training of a multi-layered neural network is proposed, which employs cone-beam CT images of many patients as input training data, and precalculated scattering projection images of the same patients as output training data. After the training is completed, scattering projection images for a new patient are estimated by inputting a cone-beam CT image of the new patient into the trained multi-layered neural network. Subsequently, scatter-free projection images for the new patient are obtained by subtracting the estimated scattering projection images from measured projection images, beam angle by beam angle. A scatter-free cone-beam CT image is reconstructed from the scatter-free projection images.

10 Claims, 8 Drawing Sheets

(56) References Cited

U.S. PATENT DOCUMENTS

| | | | | |
|---|---|---|---|---|
| 2010/0111393 A1* | 5/2010 | Okumura | ............... | A61B 6/032 |
| | | | | 378/4 |
| 2013/0051516 A1* | 2/2013 | Yang | ..................... | G06T 11/005 |
| | | | | 378/4 |
| 2013/0051519 A1* | 2/2013 | Yang | ..................... | G06T 11/005 |
| | | | | 378/19 |
| 2018/0018757 A1* | 1/2018 | Suzuki | .................. | G06T 3/4053 |

* cited by examiner

METHOD FOR RECONSTRUCTING X-RAY CONE-BEAM CT IMAGES

TECHNICAL FIELD

The present invention relates generally to a method for medical x-ray image formation, and more particularly, to an improved method for reconstructing x-ray cone-beam CT images for detecting cancers in a human body, thereby facilitating adaptive radiotherapy planning or other advanced radiotherapy planning techniques that require improved cone-beam CT image quality.

BACKGROUND ART

An x-ray cone-beam CT unit is often equipped with a radiotherapy machine for the purpose of tumor positioning inside a patient body. A typical x-ray cone-beam CT unit is described in detail in U.S. Pat. No. 6,842,502, the disclosure of which is hereby incorporated by reference. It is well known that skin marking does not provide accurate tumor positioning and the cone-beam CT facilitates more accurate tumor positioning for treating the tumor.

The x-ray beams emitted from an x-ray tube pass through the patient body and reach a flat panel detector. The flat panel detector detects not only direct x-rays but also scattered x-rays. The scattered x-rays are not required for cone-beam CT reconstruction and decrease the contrast of projection images on the detector, which means the image contrast of the cone-beam CT image reconstructed from all the projection images with various x-ray beam angles is also reduced. It is also known that the reduced image contrast of cone-beam CT images makes contouring for soft tissues more challenging. A use of grid was also proposed to reduce scattered x-rays; however, the grid could reduce less than 50% of the scattered x-rays only, and a more efficient technique was needed.

SUMMARY

The first embodiment comprises the following steps:
(1) calculating scattering component images within projection images (hereinafter, referred to as "scattering projection images") of a predetermined number of patients from predetermined x-ray beam angles,
(2) end-to-end training of a multi-layered neural network based on cone-beam CT images of predetermined number of patients as input training data and precalculated scattering projection images of the patients from predetermined x-ray beam angles as output training data,
(3) estimating scattering projection images for a new patient from predetermined beam angles by inputting a cone-beam CT image of the new patient into the trained multi-layered neural network,
(4) calculating scatter-free projection images by subtracting scattering projection images from measured projection images for predetermined x-ray beam angles, and
(5) reconstructing a scatter-free cone-beam CT image for the new patient using the scatter-free projection images.

The second embodiment comprises the following steps:
(1) calculating scattering projection images of a predetermined number of patients from predetermined x-ray beam angles,
(2) end-to-end training of a multi-layered neural network based on projection images of predetermined number of patients as input training data and precalculated scattering projection images of the patients from predetermined x-ray beam angles as output training data,
(3) estimating scattering projection images for a new patient from predetermined beam angles by inputting measured projection images of the new patient into the trained multi-layered neural network,
(4) calculating scatter-free projection images by subtracting scattering projection images from measured projection images, beam angle by beam angle, and
(5) reconstructing a scatter-free cone-beam CT image from the scatter-free projection images.

In accordance with the embodiments, scattering projection images are calculated by a Monte Carlo method or a Boltzmann's transport equation in which x-ray beams are emitted from an x-ray tube of the cone-beam CT unit and delivered to a patient body.

According to the embodiments, the calculation by a Monte Carlo method or a Boltzmann's transport equation is calibrated by a phantom experiment before subtracting each scattering projection image from each measured projection image.

In the embodiments, the following steps are further provided:
(1) placing a phantom on the treatment couch,
(2) calculating the incident x-ray intensity distributions $P(i,j)$ on the flat panel detector after the x-ray beams pass through the phantom with a known spectrum of x-ray beams emitted from the x-ray tube, where the integers of (i, j) denote coordinates on the detector,
(3) measuring incident x-ray beam intensity distributions $Q(i,j)$ on the flat panel detector,
(4) calculating a calibration factor of $A=Q_m/P_m$, where $Q_m$ and $P_m$ are spatial averages of $Q(i,j)$ and $P(i,j)$ within a predetermined area, respectively.

In accordance with the embodiments, the following steps are further provided:
(1) multiplying the estimated scattering projection images for the new patient by the calibration factor A,
(2) calculating scatter-free projection images by subtracting calibrated estimated scattering projection images from measured projection images, beam angle by beam angle, and
(3) reconstructing a scatter-free cone-beam CT image from the scatter-free projection images.

Advantages

Accordingly, several advantages of one or more aspects are as follows: to provide a reconstruction method for x-ray cone-beam CT images that gives significantly higher image contrast thereby increasing visibility of cancer tissues as well as nearby organs at risk, to provide a reconstruction method for x-ray cone-beam CT images that allows more accurate tumor positioning at the time of radiation treatment in reference to the planned position given by a treatment planning system, and to provide a reconstruction method for x-ray cone-beam CT images that allows online adaptive treatment planning based on the cone-beam CT images on each treatment day. It is known that some tumors and nearby healthy organs move day by day and therefore treatment planning needs to be created immediately before each treatment, which is called online adaptive planning and known as one of the most advanced radiotherapy techniques. Other advantages of one or more aspects will be apparent from a consideration of the drawings and ensuing description.

REFERENCE NUMERALS IN THE DRAWINGS

1 gantry head
2 collimator
5 gantry rotating mechanism
7 patient couch
9 x-ray tube
11 flat panel detector
12 grid
13 flat panel detector
15 display
20 treatment beam
22 patient
26 cone-beam for cone-beam CT imaging
28 computer
30 signal line for controlling couch movement
32 signal line for controlling the x-ray tube
34 signal line for cone-beam CT imaging
36 signal line for the flat panel detector
38 signal line for controlling treatment beams
40 cone-beam CT images of many patients for training the multi-layered neural network
41 projection images of many patients for training the multi-layered neural network
42 a multi-layered neural network
44 calculated scattering projection images using cone-beam CT images of many patients
50 cone-beam CT images of a new patient
50A projection images of the new patient
51 projection images of a new patient
52 a multi-layered neural network
54 estimated scattering projection images given as the output from the pre-trained multi-layered neural network
56 scatter-free projection images
58 a scatter-free cone-beam CT image reconstructed from scatter-free projection images

DETAILED DESCRIPTION: FIRST EMBODIMENT WITH FIGS. 1-13

Figure 1:
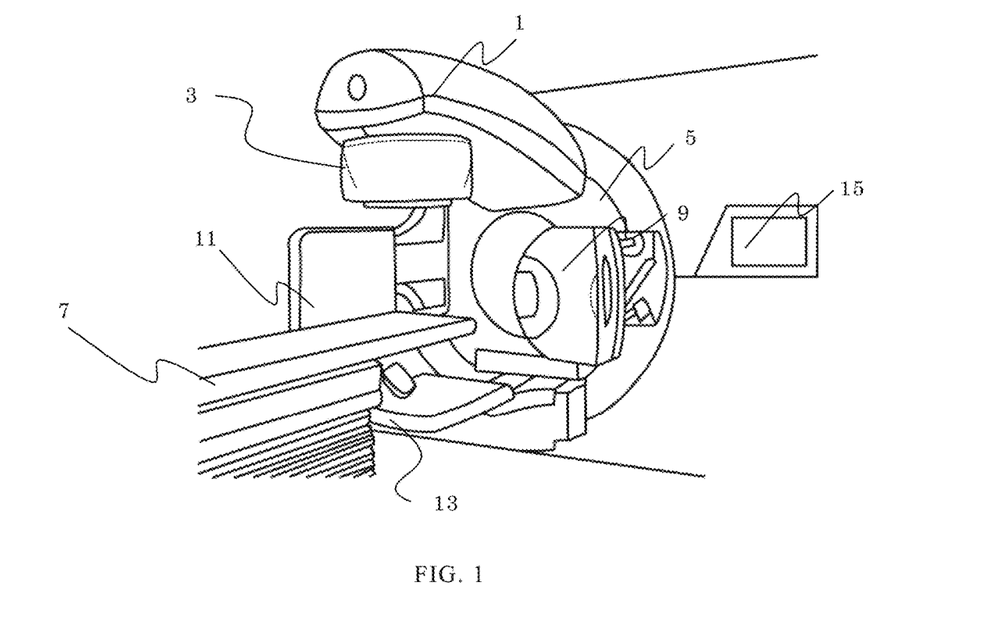
FIG. 1 is a perspective view of a radiotherapy machine equipped with an x-ray cone-beam CT unit which is used to achieve this invention.

FIG. 1 shows a perspective view of a radiotherapy machine used for this embodiment, comprising a gantry head 1 that generates treatment beams, a collimator unit 3 that shapes the treatment beam according to a tumor shape, a gantry rotating means 5, a patient couch 7 for positioning the tumor, an x-ray tube 9, a flat panel detector 11 for cone-beam CT imaging, another flat panel detector 13 for treatment beams, and a display 15 that shows the radiotherapy machine status.

Figure 2:
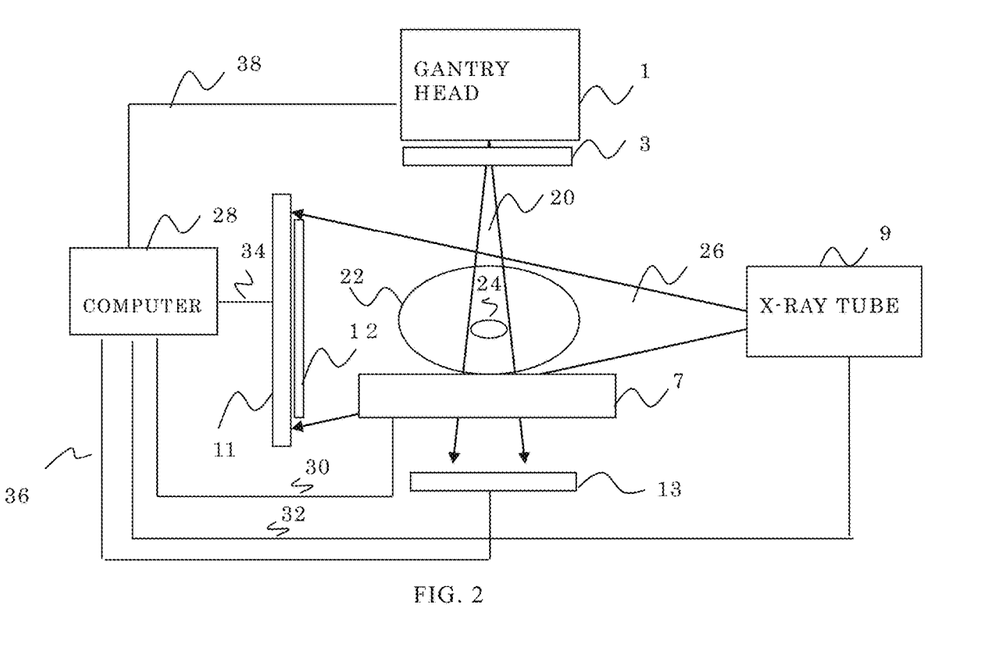
FIG. 2 is a block diagram of the machine shown in FIG. 1.

FIG. 2 depicts a block diagram of the radiotherapy machine shown in FIG. 1. A tumor 24 in a patient body 22 is placed at the position of the treatment beams by acquiring the cone-beam CT images of the patient and then moving a high-precision three-axis or six-axis patient couch. An x-ray tube 9 emits cone-shaped x-ray beams 26 towards the patient 22, and then the x-ray beams reach a flat panel detector 11 after passing an anti-scattering grid 12. By rotating the direction of the x-ray cone beams using the gantry rotating means 5 shown in FIG. 1, x-ray cone-beam CT images can be reconstructed by performing back-projection of the projection images detected on the flat panel detector 11 over the entire angles with a small beam angle spacing such as 1°. Meanwhile, the patient CT imaging is conducted using a treatment planning CT unit a week before the treatment starts. The CT data is transferred to a treatment planning system, where a treatment plan is created after contouring the tumor 24 and nearby organs at risk. By overlaying the tumor coordinates given by the treatment plan on the cone-beam CT images, the shift amount of the couch 7 is calculated and then couch repositioning is executed. Consequently, treatment beams generated in the gantry head 1 are delivered to the tumor 24 inside the patient 22 on the couch 7 after the beam is shaped by the collimator 3 according to the tumor shape.

Figure 3:
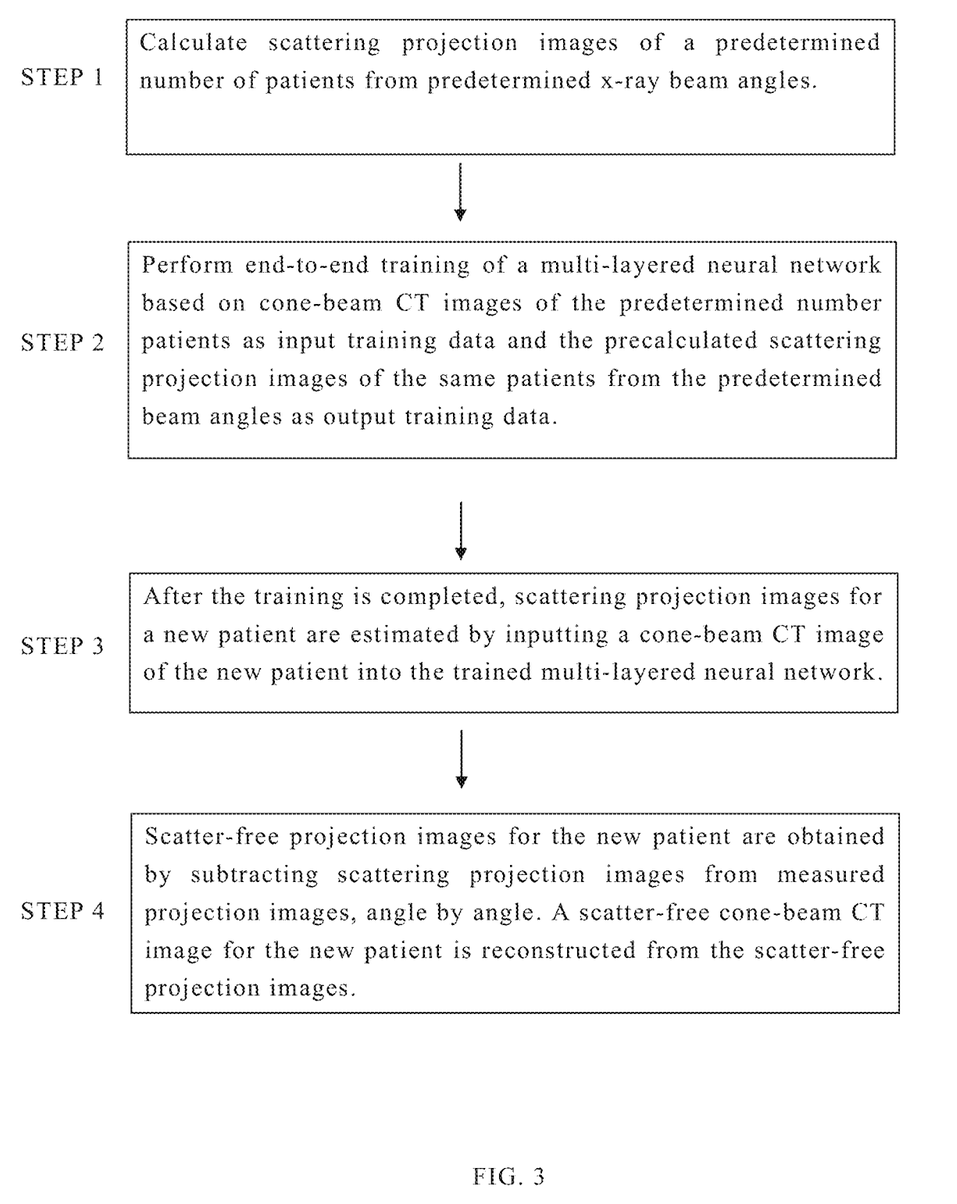
FIG. 3 is a flowchart describing an improved method for reconstructing x-ray cone-beam CT images.

FIG. 3 shows a flowchart describing an improved method for reconstructing cone-beam CT images. In STEP 1, a Monte Carlo calculation is performed to obtain scattering projection images by using cone-beam CT images of a predetermined number of patients, such as 1000 patients, for predetermined beam angles (for 3600 angles with a spacing of 10 as an example). Because the voxel values in the cone-beam CT images do not provide densities and atomic compositions, human body in the cone-beam CT images are segmented into four components of soft tissue, air, lung and bone. Subsequently typical material densities and atomic compositions are given by a published reference, thereby allowing a Monte Carlo calculation of x-ray interaction inside the human body.

In STEP 2, a multi-layered neural network is employed, where end-to-end training is performed with the cone-beam CT images of predetermined number of patients as input training data, and the scattering projection images calculated in STEP 1 as output training data.

In STEP 3, scattering projection images of a new patient over the entire beam angles with an angle spacing of 1° are estimated by inputting the cone-beam CT images of the new patient into the pre-trained multi-layered neural network.

In STEP 4, each scatter-free projection image is obtained by subtracting each scattering projection image from each measured projection image for each beam angle. A scatter-free cone-beam CT image for the new patient is reconstructed from the scatter-free projection images.

In the above STEP 1, not only the Monte Carlo calculation but also a Boltzmann's transport equation is employed for obtaining scattering projection images, where x-ray beams are emitted from an x-ray tube of the cone-beam CT unit and delivered to a patient body.

A typical end-to-end (image to label) training of a multi-layered neural network is described in detail in U.S. Pat. No. 8,504,361B2, the disclosure of which is hereby incorporated by reference. In this embodiment, detailed arithmetic is automatically created by the multi-layered neural network, where the input image and the output image are directly associated inside the neural network just like a black box, where the mathematical details are described in the above patent.

Further, a typical dose calculation method using a Monte Carlo method is described in detail in U.S. Pat. No. 6,148,272, the disclosure of which is hereby incorporated by reference. In short, the Monte Carlo method calculates each photon particle's transport from the target position inside an x-ray tube to the flat panel detector using all the physical reactions during the transport. When a large number of photons are employed during this calculation, it is known that the calculated results accurately predict measured results. Because it is not possible to directly measure scattering projection images, calculation of scattering projection images is essential in this embodiment.

In addition, a typical dose calculation method using a Boltzmann transport equation is described in detail in the following three published articles, the disclosures of which are hereby incorporated by references:

Wang A, Maslowski A, Wareing T, Star-Lack J, Schmidt T G. A fast, linear Boltzmann transport equation solver for computed tomography dose calculation (Acuros CTD). Med Phys. 2019 February; 46(2):925-933.

Wang A, Maslowski A, Messmer P, Lehmann M, Strzelecki A, Yu E, Paysan P, Brehm M, Munro P, Star-Lack J, Seghers D. Acuros CTS: A fast, linear Boltzmann transport equation solver for computed tomography scatter—Part II: System modeling, scatter correction, and optimization. Med Phys. 2018 May; 45(5):1914-1925.

Maslowski A, Wang A, Sun M, Wareing T, Davis I, Star-Lack J. Acuros CTS: A fast, linear Boltzmann transport equation solver for computed tomography scatter—Part I: Core algorithms and validation. Med Phys. 2018 May; 45(5):1899-1913.

On the other hand, a typical cone-beam CT reconstruction method is described in detail in the following publication, the disclosure of which is hereby incorporated by reference:

Feldkamp L A, Davis L C and Kress J W 1984 Practical cone-beam algorithm, J. Opt. Soc. Am. A, 1, 612-9

The above reconstruction technique is known as Feldkamp's back-projection; in other words, projection images from every different angles are back-projected to obtain a cone-beam CT image, which is widely used in industrial and medical fields.

Figure 4:
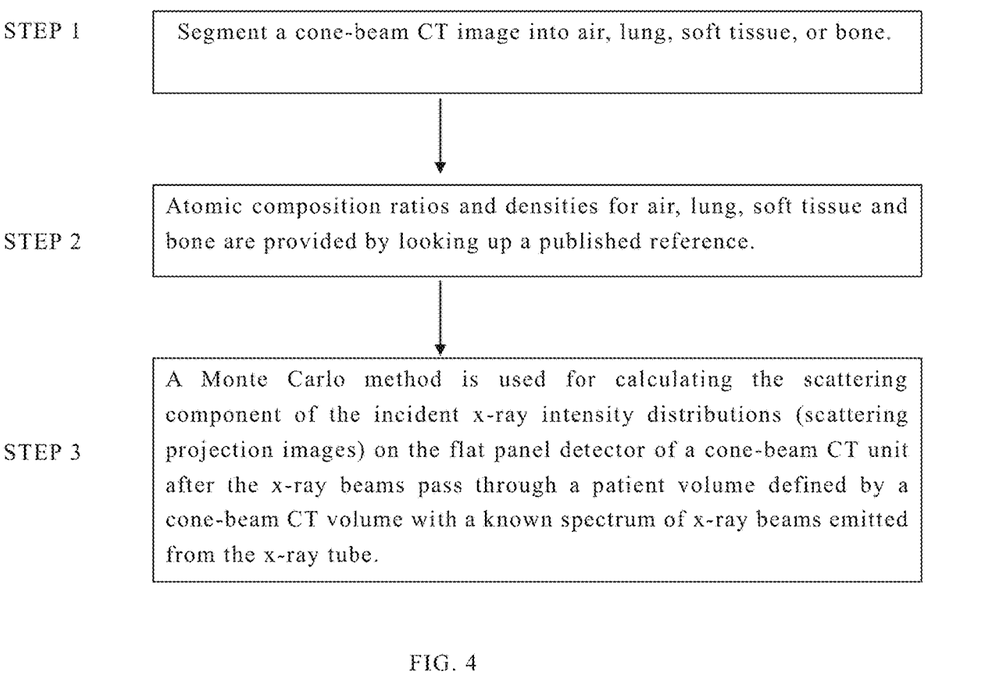
FIG. 4 is a flowchart describing a method for calculating scattering projection images.

FIG. 4 shows a flowchart for calculating scattering projection images by a Monte Carlo method. In STEP 1, a cone-beam CT image is segmented into either of air, lung, soft tissue, or bone. In STEP 2, densities and atomic compositions of the air, lung, soft tissue, and bone are given by referring to a published article in 1989, entitled 'Tissue Substitutes in Radiation Dosimetry and Measurement' as Report 44 of the International Commission on Radiation Units and Measurements. In STEP 3, a Monte Carlo method is used for calculating the scattering component of the incident x-ray intensity distributions (namely, scattering projection image) on the flat panel detector for the cone-beam CT after the x-ray beams pass through a patient volume specified by a cone-beam CT image with a known spectrum of x-ray beams emitted from the x-ray tube. A Monte Carlo code, EGS is employed in this embodiment, but other Monte Carlo codes including GEANT and PHITS can also be used.

Figure 5:
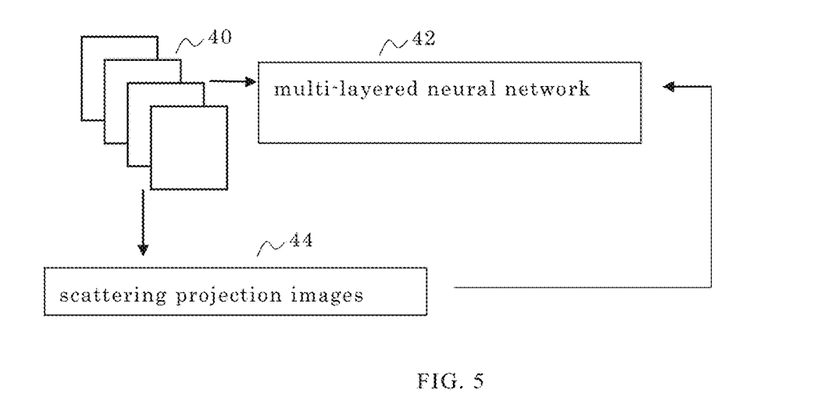
FIG. 5 is a block diagram showing an end-to-end training process using a multi-layered neural network, with input training data of cone-beam CT images of a predetermined number of patients, and output training data of pre-calculated scattering projection images of the patients.

FIG. 5 shows a block diagram of the end-to-end training using a multi-layered neural network 42 as also described in the STEP 2 of FIG. 3. Cone-beam CT images 40 of a predetermined number of patients, such as 1000 patients, are used as input training data, whilst scattering projection images 44 in every degree of beam angles are employed as output training data. The scattering projection images are calculated by a Monte Carlo method or Boltzmann's transport equation based on the same patient's cone-beam CT images as shown in FIG. 4. This type of end-to-end training is also referred to as end-to-end deep learning which has been widely used in industrial and medical fields.

Figure 6:
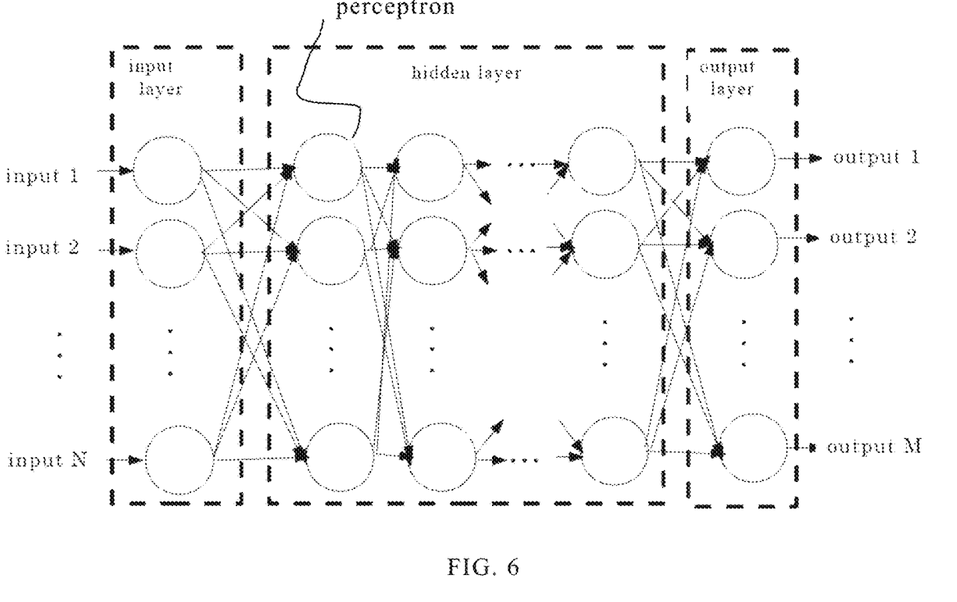
FIG. 6 is a diagram of multi-layered neural network used for the end-to-end training.

FIG. 6 depicts a structure of the multi-layered neural network, which includes an input layer, an output layer, and a hidden layer. The hidden layer usually have four or more sub-layers, and each layer has perceptrons having input and output nodes. During training (in other words, deep learning), the weights of the perceptrons are optimized to best model the input and output relationships.

Figure 7:
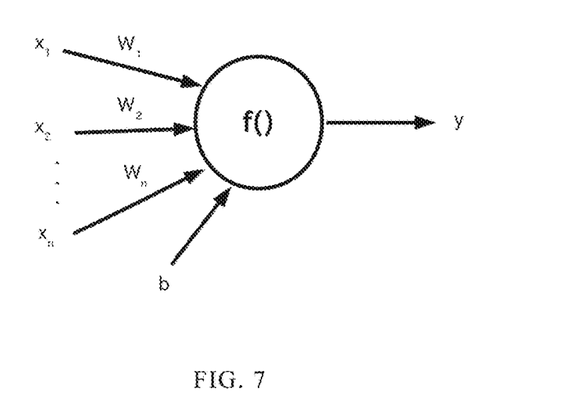
FIG. 7 is a diagram showing the structure of each perceptron shown in FIG. 6.

FIG. 7 shows a typical perceptron having input nodes of $x_1, x_2, \ldots$, an output node of y, and a bias node of b, where y is given by $f(w_1 x_1 + w_2 x_2 + \ldots) + b$, and f is a non-linear function. The weights $w_i$'s are determined by iterative optimization with a large number of input and output data combination. After the training is completed, an output corresponding to a new input is instantaneously obtained by the trained neural network.

Figure 8:
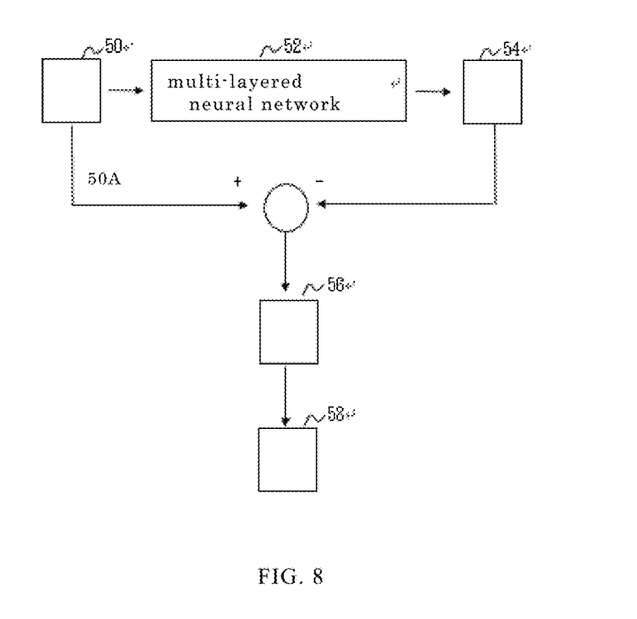
FIG. 8 is a procedure of calculating scatter-free cone-beam CT images, wherein a measured cone-beam CT image of a new patient is fed into the pre-trained multi-layered neural network. A set of scattering projection images are obtained as output. Subtracting the scattering projection images from measured projection images results in scatter-free projection images, from which a scatter-free cone-beam CT image of the new patient is reconstructed.

FIG. 8 demonstrates a procedure for estimating scatter-free cone-beam CT images for a new patient, wherein a measured cone-beam CT image 50 of the new patient is fed into the pre-trained multi-layered neural network 52. A set of scattering projection images 54 are obtained as output. Subtracting the scattering projection images 54 from the measured projection images 50A results in scatter-free projection images 56, from which scatter-free cone-beam CT images 58 are reconstructed.

Figure 9:
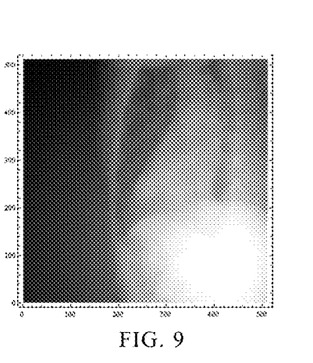
FIG. 9 is a measured projection image for a new patient.
Figure 10:
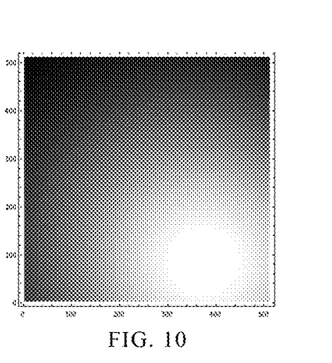
FIG. 10 is a scattering projection image for the new patient which is estimated by inputting the patient's cone-beam CT image into the pre-trained neural network.
Figure 11:
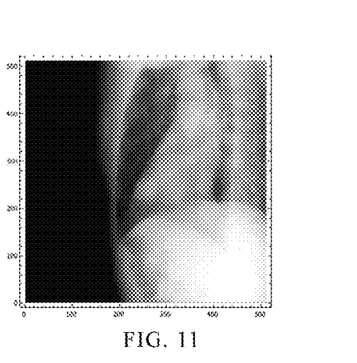
FIG. 11 is a scatter-free projection image calculated by subtracting the estimated scattering projection image shown in FIG. 10 from the measured projection image shown in FIG. 9.

Examples of the measured projection images 50A, scattering projection images 54, and scatter-free projection images 56 in chest region are shown in FIG. 9, FIG. 10, and FIG. 11, respectively.

Figure 12:
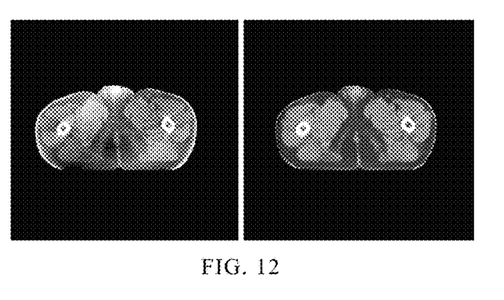
FIG. 12 shows a pair of cone-beam CT images before applying this invention (on the left) and that after applying this invention (on the right)

FIG. 12 also shows an example in abdominal region, where an original cone-beam CT image is on the left whereas a scatter-free cone-beam CT image as a result of this embodiment is on the right.

Figure 13:
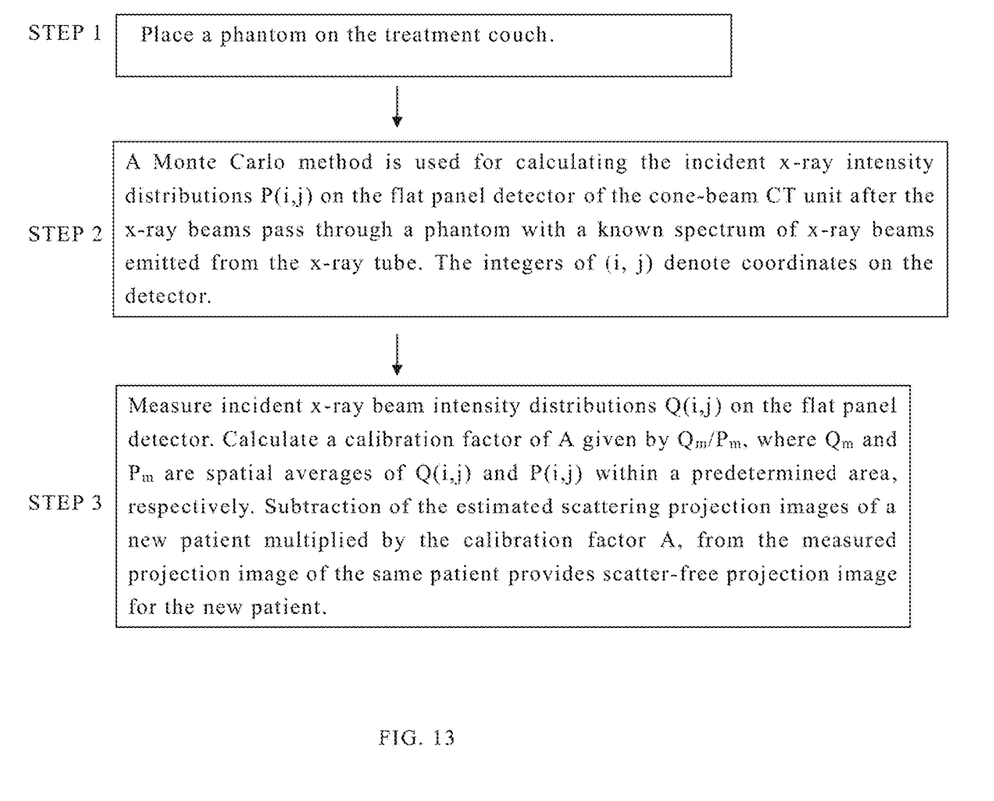
FIG. 13 is a flowchart showing the calibration procedure between the measurement and the calculation of the projection images.

FIG. 13 is a flowchart showing a calibration procedure between the measurement and the calculation. This is required because the calculated results by the Monte Carlo method or the Boltzmann transport equation have an arbitrary scaling factor and therefore it needs to be calibrated against the measurement. Once the calculation is calibrated, then it is possible to subtract the scattering projection images from the measured projection images. In STEP 1, a phantom is placed on the treatment couch.

In STEP 2, a Monte Carlo method is used for calculating the incident x-ray intensity distributions P(i,j) on the flat panel detector of the cone-beam CT unit after the x-ray beams pass through a phantom volume with a known spectrum of x-ray beams emitted from the x-ray tube. The integers of (i, j) denote coordinates on the detector. The calculated incident x-ray intensity distributions P(i,j) contain both direct x-ray and scattered x-ray contributions; and therefore, they can be compared to measured x-ray distributions on the detector for the calibration purpose. The order of executing the STEP 1 and the STEP 2 of FIG. 13 can be reversed as they are independent.

In STEP 3, the flat panel detector reads incident beam intensity distributions Q(i,j) with the phantom on the couch. Subsequently, a calibration factor A is defined by Qm/Pm where $Q_m$ and $P_m$ are spatial averages of Q(i,j) and P(i,j) within a predetermined central area, such as 10×10 cm², respectively. Subtraction of the estimated scattering projection images of a new patient multiplied by the calibration factor A, from the measured projection image of the same patient provides scatter-free projection images.

In the above embodiment, cone-beam CT images of the patients are employed as input training data of the multi-layered neural network. It is also possible to use projection images of all the patients' cone-beam CT images as input data, which will be described in the second embodiment below. The same procedures are used also in the second embodiment as those described in the first embodiment except for this difference. Because of this, some detailed procedures in the second embodiment are not repeatedly disclosed to avoid redundancy. The scope of the second embodiment should therefore be determined by the appended claims.

DETAILED DESCRIPTION: SECOND EMBODIMENT WITH FIGS. 14-16

Figure 14:
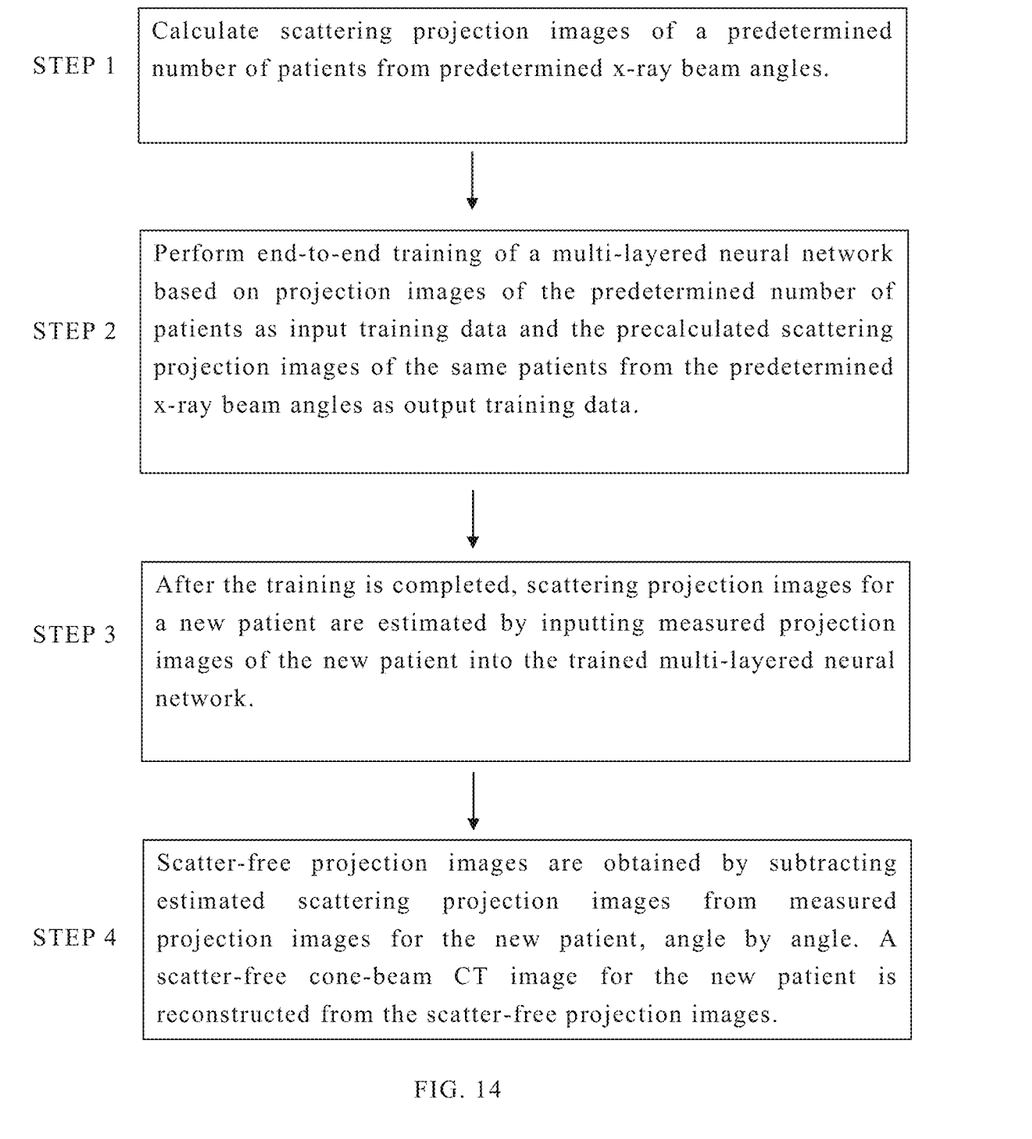
FIG. 14 is another flowchart describing another embodiment of this invention that results in improved x-ray cone-beam CT images.

FIG. 14 is another flowchart that results in improved x-ray cone-beam CT images. In STEP 1, scattering projection images of a predetermined number of patients are calculated from predetermined beam angles.

In STEP 2, end-to-end training of a multi-layered neural network is performed, based on projection images of the predetermined number of patients as input and the precalculated scattering projection images of the same patients from predetermined beam angles as output. The input and output pair for the training is chosen patient by patient.

In STEP 3, After the training is completed, scattering projection images for a new patient are estimated by inputting projection images of the new patient into the trained multi-layered neural network.

In STEP 4, Scatter-free projection images are obtained by subtracting scattering projection images from measured projection images, beam angle by beam angle. A scatter-free cone-beam CT image is reconstructed from the scatter-free projection images.

Figure 15:
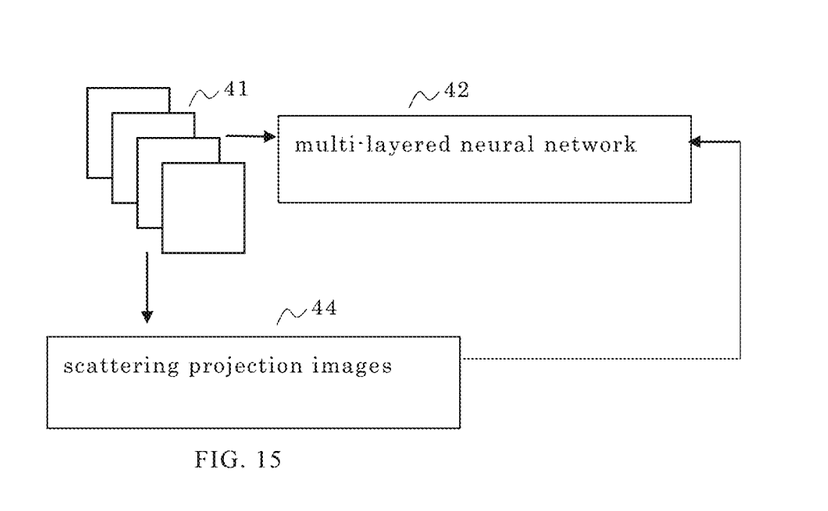
FIG. 15 is another block diagram showing a slightly different end-to-end training of a multi-layered neural network, wherein the input training data are given by measured projection images instead of a measured cone-beam CT image.

FIG. 15 shows another block diagram showing a slightly different end-to-end training of a multi-layered neural network 42, where the difference is input data only; in other words, projection images of many patients 41 are employed rather than cone-beam CT images of many patients.

Figure 16:
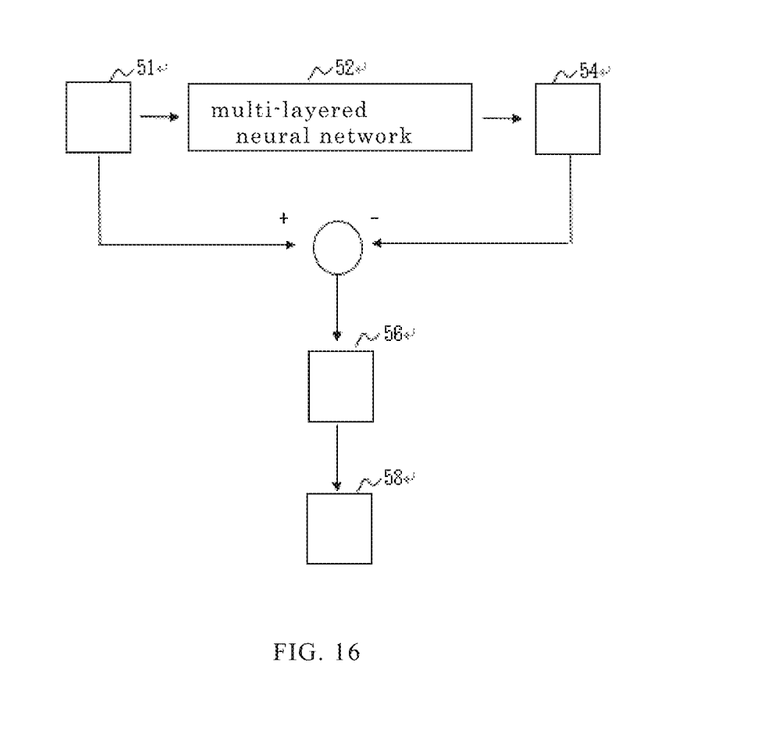
FIG. 16 is another procedure for estimating scatter-free cone-beam CT images, wherein measured projection images of a new patient are fed into the pretrained multi-layered neural network. A set of scattering projection images are obtained as output. Subtracting the scattering projection images from the measured projection images results in scatter-free projection images, from which a scatter-free cone-beam CT image of the new patient is reconstructed.

FIG. 16 shows another procedure for estimating a scatter-free cone-beam CT image for a new patient, wherein projection images 51 of a measured cone-beam CT image are fed into the pre-trained multi-layered neural network 52. Then, scattering projection images 54 for the new patient are estimated as output. Subtracting the estimated scattering projection images 54 from the measured projection images 51 results in scatter-free projection images 58, from which a scatter-free cone-beam CT image of the new patent is reconstructed. It is noted that calibration between the calculation and the measurement needs to be performed before the subtraction procedure as was described in the first embodiment. In other words, in practice, subtracting the estimated scattering projection images 54 multiplied by the calibration factor A, from the measured projection images 51 results in scatter-free projection images 58.

Although the description above contains many specificities, these should not be construed as limiting the scope of the embodiments but as merely providing illustrations of some of several embodiments. For example, the above embodiments can also include a grid that physically reduces scattering 50% at the best. Lastly, the scope of the embodiments should be determined by the appended claims and their legal equivalents, rather than by the examples given.

What is claimed is:

1. A method for reconstructing x-ray cone-beam CT images, comprising:
   (a) calculating scattering projection images of a predetermined number of patients from predetermined x-ray beam angles using measured cone-beam CT images of said patients;
   (b) end-to-end training of a multi-layered neural network based on said measured cone-beam CT images of said patients as input training data, and the calculated scattering projection images of said patients from said predetermined x-ray beam angles as output training data;
   (c) estimating scattering projection images for a new patient by inputting a measured cone-beam CT image of said new patient into the trained multi-layered neural network;
   (d) calculating scatter-free projection images for said new patient, beam angle by beam angle, by subtracting said scattering projection images for said new patient, from measured projection images for said new patient, and reconstructing a scatter-free cone-beam CT image for said new patient from said scatter-free projection images for said new patient,
      whereby said scatter-free cone-beam CT image has an improved contrast thus facilitating more accurate tumor and organ contouring, more accurate tumor positioning, and online adaptive radiotherapy.

2. The method of claim 1, wherein said scattering projection images are calculated by a Monte Carlo method or Boltzmann's transport equation.

3. The method of claim 1, wherein the calculation is calibrated against the measurement before the subtracting operation.

4. The method of claim 1, further comprising:
placing a phantom on a treatment couch;
calculating incident x-ray intensity distributions P(i,j) on the flat panel detector of the cone-beam CT unit after the x-ray beams pass through said phantom with a known spectrum of x-ray beams emitted from an x-ray tube, where the integers of (i, j) denote coordinates on the detector;
measuring incident x-ray beam intensity distributions Q(i,j) on said flat panel detector with said phantom on said couch;
calculating a calibration factor of A given by $Q_m/P_m$, where $Q_m$ and $P_m$ are spatial averages of Q(i,j) and P(i,j) within a predetermined area, respectively.

5. The method of claim 1, further comprising:
multiplying said scattering projection images for said new patient by said calibration factor A, which is referred to as calibrated scattering projection images;
calculating scatter-free projection images by subtracting said calibrated scattering projection images from said measured projection images.

6. A method for reconstructing x-ray cone-beam CT images, comprising:
(a) calculating scattering projection images of a predetermined number of patients from predetermined x-ray beam angles using measured cone-beam CT images of said patients;
(b) end-to-end training of a multi-layered neural network based on measured projection images of said patients as input training data and the calculated scattering projection images of said patients from said predetermined x-ray beam angles as output training data,
(c) estimating scattering projection images for a new patient by inputting measured projection images of said new patient into the trained multi-layered neural network,
(d) calculating scatter-free projection images for said new patient, beam angle by beam angle, by subtracting said scattering projection images for said new patient, from measured projection images for said new patient, and reconstructing a scatter-free cone-beam CT image for said new patient from said scatter-free projection images for said new patient,
whereby said scatter-free cone-beam CT image has an improved contrast thus facilitating more accurate tumor and organ contouring, more accurate tumor positioning, and online adaptive radiotherapy.

7. The method of claim 6, wherein said scattering projection images are calculated by a Monte Carlo method or Boltzmann's transport equation.

8. The method of claim 6, wherein the calculation is calibrated against the measurement before the subtracting operation.

9. The method of claim 6, further comprising:
placing a phantom on a treatment couch;
calculating incident x-ray intensity distributions P(i,j) on the flat panel detector of the cone-beam CT unit after the x-ray beams pass through said phantom with a known spectrum of x-ray beams emitted from an x-ray tube, where the integers of (i, j) denote coordinates on the detector;
measuring incident x-ray beam intensity distributions Q(i,j) on said flat panel detector with said phantom on said couch;
calculating a calibration factor of A given by $Q_m/P_m$, where $Q_m$ and $P_m$ are spatial averages of Q(i,j) and P(i,j) within a predetermined area, respectively.

10. The method of claim 6, further comprising:
multiplying said scattering projection images for said new patient by said calibration factor A, which is referred to as calibrated scattering projection images;
calculating scatter-free projection images by subtracting said calibrated scattering projection images from said measured projection images.

* * * * *